(12) United States Patent
Marozas et al.

(10) Patent No.: US 12,369,839 B2
(45) Date of Patent: Jul. 29, 2025

(54) LONG-TERM NON-INVASIVE SYSTEM FOR MONITORING AND CHARACTERIZING ATRIAL ARRHYTHMIAS IN PATIENTS WITH POST-STROKE CONDITIONS

(71) Applicants: Kaunas University of Technology, Kaunas (LT); Vilnius University, Vilnius (LT)

(72) Inventors: Vaidotas Marozas, Kaunas (LT); Andrius Petrenas, Kaunas (LT); Andrius Solosenko, Kaunas (LT); Saulius Daukantas, Kaunas (LT); Monika Simaityte, Kaunas (LT); Andrius Rapalis, Kaunas (LT); Justinas Bacevicius, Vilnius (LT); Audrius Aidietis, Didzioji Riese (LT)

(73) Assignee: Kaunas University of Technology, Kaunas (LT)

( * ) Notice: Subject to any disclaimer, the term of this patent is extended or adjusted under 35 U.S.C. 154(b) by 683 days.

(21) Appl. No.: 17/295,469

(22) PCT Filed: Nov. 21, 2019

(86) PCT No.: PCT/IB2019/060028
§ 371 (c)(1),
(2) Date: May 20, 2021

(87) PCT Pub. No.: WO2020/104986
PCT Pub. Date: May 28, 2020

(65) Prior Publication Data
US 2022/0015683 A1     Jan. 20, 2022

(30) Foreign Application Priority Data
Nov. 22, 2018    (LT) .................................. PA 2018 550

(51) Int. Cl.
*A61B 5/364*   (2021.01)
*A61B 5/00*   (2006.01)
(Continued)

(52) U.S. Cl.
CPC .......... *A61B 5/364* (2021.01); *A61B 5/02416* (2013.01); *A61B 5/257* (2021.01);
(Continued)

(58) Field of Classification Search
CPC ... A61B 5/6815; A61B 5/6831; A61B 5/6823; A61B 5/6826; A61B 5/6828; A61B 5/364; A61B 5/318; A61B 5/333; A61B 5/02416
See application file for complete search history.

(56) References Cited

U.S. PATENT DOCUMENTS 6,519,490 B1   2/2003   Wiesel
7,794,406 B2   9/2010   Reisfeld et al.
(Continued)

FOREIGN PATENT DOCUMENTS

| WO | WO-2010079257 A1 * | 7/2010 | ........... A61B 5/0205 |
| WO | WO-2011074004 A2 * | 6/2011 | ........... A61B 5/0006 |
| WO | 20170124946 A1 | 7/2017 | |

OTHER PUBLICATIONS

International Search Report and Written Opinion mailed Nov. 23, 2020 for PCT Application No. PCT/IB2018/060028.
(Continued)

*Primary Examiner* — John D Li
(74) *Attorney, Agent, or Firm* — Koivula & Somersalo, LLC (57) ABSTRACT

The system and method defined herein are intended to detect, monitor and characterize in a non-invasive way cardiac arrhythmias of a patient that are associated with the development of atrial arrhythmia and increased risk of
(Continued)

ischemic cerebral stroke. The system consists of a portable device with integrated sensors for biosignals; integrated modules in the portable device for recognition of intermittent atrial arrhythmia episodes; a module for characterization of the distribution of atrial arrhythmia episodes aiming to assess disease progression. The proposed is a technical solution allows for long-term monitoring of atrial fibrillation in a non-invasive way for the patient. If a non-documented atrial arrhythmia is detected by automatic means during the long-term monitoring, a physician is informed by e-mail by sending the electrocardiogram of the said arrhythmia episode. If the physician confirms diagnosis of atrial fibrillation, a recommendation for immediate medical attention is sent to patient's smart device.

13 Claims, 4 Drawing Sheets

(51) Int. Cl.
    *A61B 5/024*     (2006.01)
    *A61B 5/257*     (2021.01)
    *A61B 5/318*     (2021.01)
    *A61B 5/333*     (2021.01)

(52) U.S. Cl.
    CPC .............. *A61B 5/318* (2021.01); *A61B 5/333* (2021.01); *A61B 5/6815* (2013.01); *A61B 5/6823* (2013.01); *A61B 5/6826* (2013.01); *A61B 5/6828* (2013.01); *A61B 5/6831* (2013.01)

(56) References Cited

U.S. PATENT DOCUMENTS

| | | | |
|---|---|---|---|
| 2002/0147409 A1 | 10/2002 | Baker et al. | |
| 2005/0192503 A1* | 9/2005 | Sula | A61B 5/327 600/509 |
| 2007/0255146 A1 | 11/2007 | Andrews et al. | |
| 2010/0268103 A1* | 10/2010 | McNamara | G16H 15/00 600/523 |
| 2013/0274623 A1* | 10/2013 | Zhang | A61B 5/349 600/517 |
| 2015/0018693 A1 | 1/2015 | Mestha et al. | |
| 2015/0164349 A1* | 6/2015 | Gopalakrishnan | A61B 5/746 600/508 |
| 2015/0366518 A1 | 12/2015 | Sampson | |
| 2016/0235325 A1* | 8/2016 | Chou | A61B 5/6826 |
| 2016/0331247 A1 | 11/2016 | Albert et al. | |
| 2017/0014037 A1* | 1/2017 | Coppola | A61B 5/02416 |
| 2017/0202459 A1 | 7/2017 | Cao | |
| 2018/0064356 A1* | 3/2018 | Mendenhall | G16H 40/67 |

OTHER PUBLICATIONS

Lee J. et al. Atrial fibrillation detection using an iphone 4S, IEEE Transactions on Biomedical Engineering, 60(1), 203-206, 2013.

Couderc J. P. et al. Detection of atrial fibrillation using contactless facial video monitoring Heart Rhythm, 12(1 ), 195-201 , 2015.

Conroy T. et al. Detection of atrial fibrillation using an earlobe photoplethysmographic sensor, Physiological Measurement, 38(10), 1906, 2017.

Corino V. D. A. et al. Detection of atrial fibrillation episodes using a wristband device, Physiological Measurement, 38 (5), 787, 2017.

Charitos E.I. et al. A comprehensive evaluation of rhythm monitoring strategies for the detection of atrial fibrillation recurrence: insights from 647 continuously monitored patients and implications for monitoring after therapeutic Interventions, Circulation, 126(7), 806-814, 2012.

Yang, Sheng-Yi, "Atrial fibrillation burden and the risk of stroke: A systematic review and dose-response meta-analysis," World Journal of Clinical Cases, ISSN 2307-8960 (online); 10(3): 939-953, Jan. 21, 2022.

Bacevicius, Justinas, "High Specificity Wearable Device with Photoplethysmography and Six-Lead Electrocardiogramatrial Fibrillation Detection Challenged by Frequent Premature Contractions: DoubleCheck-AF," Frontiers in Cardiovascular Medicine, doi: 10.3389/fcvm.2022.86930, Apr. 6, 2022.

Butkuvienė, Monika, "Characterization of Atrial Fibrillation Episode Patterns: A Comparative Study," LOGO IEEE Transactions of Biomedical Engineering, vol. XX, No. XX, XXXX 2023, DOI 10.1109/TBME.2023.3293252.

* cited by examiner

LONG-TERM NON-INVASIVE SYSTEM FOR MONITORING AND CHARACTERIZING ATRIAL ARRHYTHMIAS IN PATIENTS WITH POST-STROKE CONDITIONS

FIELD OF THE INVENTION

The invention belongs to the field of medical equipment, and specifically—a system and method for the extended time monitoring of arrhythmia episodes and characterisation of distribution of arrhythmia episodes in the post stroke patients in an unobtrusive way.

BACKGROUND OF THE INVENTION

A system and a method hereby described are intended to detect, to monitor and to characterise the cardiac arrhythmias (further—atrial arrhythmias) that are associated with the development of atrial fibrillation and increased risk of ischemic cerebral stroke. The system consists of a wearable device with integrated sensors of biosignals (photoplethysmogram, electrocardiogram, bioimpedance, temperature, moisture, movements), modules for self-intermittent episodes of atrial arrhythmia, covering permanent monitoring of photoplethysmogram and a short-term electrocardiogram, intended for integration in the wearable device; a module to assess characterisation of the distribution of arrhythmia episodes to assess disease progression, to be used in a server, in a personal computer or a smart devise (such as smart phone, a tablet or a smart watch, etc.). The presented solution allows to perform a long-term patient's atrial arrhythmia monitoring in an unobtrusive way, therefore can be used both in healthcare establishments and at patient's home.

A standard out-patient electrocardiogram recording devices with sticky electrodes (e.g. Holter monitors, Cardiac event monitors) were used aiming to recognise spontaneously terminating and often asymptomatic arrhythmias. The progress in electronics and medical technologies during the current years has offered possibilities to recognise rhythm disorders by using methods that involve minimal contact and are more convenient for the patient, such as photoplethysmography. The first applications of photoplethysmography were limited to the feasibility studies of atrial fibrillation detection when the signals were recorded by a smart phone (Lee J. et al. Atrial fibrillation detection using an iPhone 4S, IEEE Transactions on Biomedical Engineering, 60(1), 203-206, 2013), internet camera (Couderc J. P. et al. Detection of atrial fibrillation using contactless facial video monitoring Heart Rhythm, 12(1), 195-201, 2015), ear sensor (Conroy T. et al. Detection of atrial fibrillation using an earlobe photoplethysmographic sensor, Physiological Measurement, 38(10), 1906, 2017), or a smart bracelet (Corino V. D. A. et al. Detection of atrial fibrillation episodes using a wristband device, Physiological Measurement, 38(5), 787, 2017). The efficacy of these methods is still significantly behind the results obtained using the standard electrocardiography-based method. This is explained by low quality of photoplethysmography signal due to movement artefact as compared with electrocardiogram signals and by the absence of reliable specific methods for the processing of photoplethysmography signals.

The devices designed for the assessment of cardiac activity by analysing photoplethysmographic waveform usually are intended for a long-term wear and are attached to one of patient's limbs (U.S. Pat. No. 6,519,490 B1, US 2007/0255146, U.S. Pat. No. 7,794,406 B2, US 2015/0018693 A1). Document U.S. Pat. No. 6,519,490 B1 (published on 11 Feb. 2003) describes methods for detection of atrial fibrillation by using devices able to record pulse waveforms (such as a cuff of blood pressure measuring devices recording pressure waveforms). The method is based on the analysis of time sequences between the successive ventricular contractions, which allow to identify atrial fibrillation related cardiac rhythm disorder. The pressure pulse waveforms recorded by these devices are comparatively short <30, therefore reliability of arrhythmia detection algorithm is not high. Document US 2007/0255146 (published on 1 Nov. 2007) describes the system and methods to detect atrial fibrillation in the photoplethysmographic waveform by using photoplethysmographic sensor attached to the patient's finger. A finger photoplethysmographic sensor causes discomfort, therefore such method is not suitable for a long-term patient monitoring aiming to detect spontaneously terminating episodes of atrial fibrillation. Document U.S. Pat. No. 7,794,406 B2 (published on 14 Jan. 2010) describes the photoplethysmography-based bracelet-type device designed for the assessment of pulse and blood saturation with oxygen, breathing rate and heart rhythm disorders (such as premature ventricular contractions). This bracelet type system is designed to collect data from the external sensors—integration of sensors has not been foreseen in the bracelet. Document US 2015/0018693 A1 (published on 15 Jan. 2015) describes the configuration of photoplethysmography sensors in the bracelet, designed for detection of atrial fibrillation with higher reliability. Photoplethysmographic signals are recorded by several individual sensors from the selected body part (e.g., finger, wrist, tight, calve). The system foresees a possibility for arrhythmia alarm, when alarm message is sent by SMS, e-mail or by informing the patient using an audio signal. All above discussed methods and systems do not foresee the possibility to specify the diagnosis by electrocardiogram recording.

The devices offering photoplethysmogram and electrocardiogram recording were suggested to overcome the above-mentioned limitations (US 2015/0164349 A1, US 2016/0331247 A1, US 2017/0202459 A1, US 2015/0366518 A1). Document US 2015/0164349 A1 (published on 18 Jun. 2015) describes the system and methods designed to assess heart rhythm, heart rhythm variability and to detect arrhythmias (e.g., atrial fibrillation). This system also provides rating of heart condition in points as well as targets and recommendations for the user. During the use of this system the sensors integrated in the bracelet continuously record pulse and alarm is activated when irregularity of cardiac rhythm is detected aiming to inform the system user to record electrocardiogram using an external device. Different devices can be used as an external electrocardiogram recording device, e.g. a case of a smart phone with integrated electrodes of bioelectric potentials, out-patient or clinical electrocardiogram recorder, etc. The system does not offer an option to register the signal intended for diagnosis specification by the bracelet without using the external device. This limitation has been overcome in the extended system described in document US 2016/0331247 A1 (published on 17 Nov. 2016), offering the option of electrocardiogram electrodes integration into the bracelet, wherein one electrode has continuous contact with hand and another should be touched with the finger of the opposite hand. In this system a photoplethysmography justified arrhythmia detection algorithm is based on the analysis of heart rate deviation from the normal range, therefore it is sensitive to false alarms caused by different physiological factors, which can cause a sudden increase of heart rate (e.g. emotional stress). Moreover, registration of electrocardiogram signal by the system is limited to 1 derivation only, which reduces reliability of arrhythmia diagnosis.

Document US 2015/0366518 A1 (published on 24 Dec. 2015) describes methods and a system designed to detect significant and health threatening situations (e.g. imminent myocardial infarction) and to alert individuals. The system records photoplethysmogram, accelerometer and, if needed, a short-time electrocardiogram signal. Different device modifications have been described including both bracelets and glasses with integrated photoplethysmogram sensors. The system allows activation of "panic" regimen and remote assistance call (such as emergency service, police, a fire service, etc.). Unusual solution for biosignal recording has been suggested in document US 2017/0202459 A1 (published on 20 Jul. 2017), offering registration of photoplethysmogram by a sensor integrated in a headphone, and registration of electrocardiogram between an ear and a hand. Synchronous registration of electrocardiogram and photoplethysmogram offers an option to assess the time of pulse waveform spread and to present a surrogate value of permanent blood pressure. All above listed methods and systems are not designed for the detection of atrial arrhythmia of other types and do not offer a possibility for characterisation of atrial arrhythmia episodes.

It was suggested to assess the time distribution of the atrial fibrillation episodes by arrhythmia density parameter, which takes into account a profile of arrhythmia episodes distribution and indicates whether the arrhythmia episodes are evenly distributed through the entire monitoring period or are aggregated in a certain period (Charitos E. I. et al. A comprehensive evaluation of rhythm monitoring strategies for the detection of atrial fibrillation recurrence: insights from 647 continuously monitored patients and implications for monitoring after therapeutic interventions, Circulation, 126(7), 806-814, 2012). The suggested parameter of atrial fibrillation density has some limitations as a single arrhythmia episode recorded within the entire monitoring period obtains the maximal density value irrespective of its duration.

Spontaneously terminating atrial fibrillation episodes can last from several seconds to several days, therefore such method distorts results of arrhythmia episode profile characterisation. Moreover, the suggested method is applicable to characterise atrial fibrillation arrhythmia only and does not offer any opportunity to combine several arrhythmia types, which would allow to assess a progress of arrhythmia development into more complicated stages.

As compared with the solution disclosed in this description, the following limitations were reported in the state of art solutions:
   the suggested systems after detecting in a photoplethysmogram an atrial arrhythmia of an individual type do not have any possibilities to alert the device user in a real time and to record a short-term electrocardiogram signal, which would be used by a physician to confirm or reject an initial diagnosis made by automated means,
   the descriptions of suggested systems do not specify any methods based of photoplethysmogram signals allowing in a real time to detect atrial arrhythmias of different types,
   the descriptions of presented patents do not specify any methods used to characterise a time distribution of atrial arrhythmias.

A technical solution suggested in this description is free of the above listed limitations.

SUMMARY OF THE INVENTION

Embodiment disclosed in this description is a system and a method for detection and long-term monitoring of atrial arrhythmias as well as characterisation of a time distribution of atrial arrhythmias. A system is designed for the preventive examination of healthy individuals and those with increased risk of atrial arrhythmia. Monitoring can be carried out in different ways: e.g. during the treatment in out-patient setting; in the rehabilitation and nursing hospitals, i the day or long-term treatment hospital, in the private healthcare establishments, which could provide atrial arrhythmia monitoring services for their patients; also for the patients after severe illness (e.g. cerebral stroke, myocardial infarction, patients on dialysis treatment), in patients with increased risk of atrial fibrillation and stroke; for clinics responsible for personalised selection of antiarrhythmic medication doses; in clinics carrying out post-procedural prognostic indication and efficacy evaluation of therapeutic interventions (such as catheter ablation); for pharmaceutical enterprises conducting a long term studies of medicinal preparations.

The embodiment consisting of a portable patient coupled device with integrated modules for a real time detection of atrial arrhythmia; server software modules designed to characterise a time distribution of atrial arrhythmia episodes; a smart device used by a physician (e.g. a smartphone, a tablet computer, a smartwatch etc.) or personal computer designed to analyse the summarised results. Data from patients' home are transferred applying cloud technologies and utilising a patient's smart device. If a non-documented atrial arrhythmia, especially an atrial fibrillation is detected by automatic means during the long-term monitoring, a physician is informed by e-mail by sending the electrocardiogram of the said arrhythmia episode. If the physician confirms the diagnosis of atrial fibrillation, a recommendation to seek the advice of cardiologist is sent to patient's smart device.

BRIEF DESCRIPTION OF THE FIGURES

The embodiments for system implementation are described below with the references to enclosed drawings which.

The presented figures are intended for illustration purposes, their scale, proportions and other aspects not necessarily corresponds to the real technical solution.

DETAILED DESCRIPTION OF THE INVENTION

Figure 1:
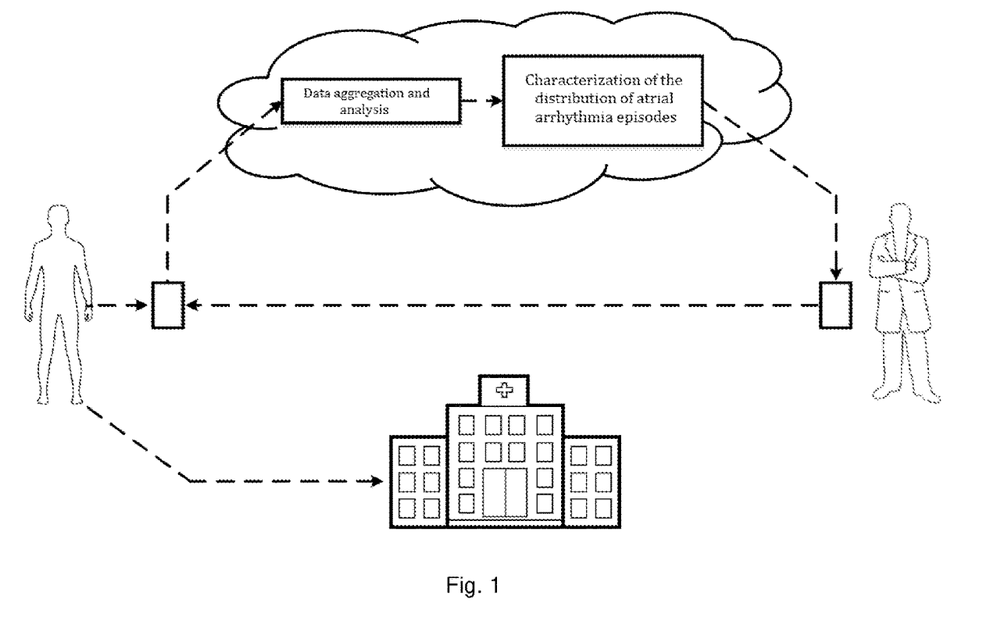
FIG. 1. Illustrates a scheme of reciprocity between the main components of the system.

Application of the system described herein is not limited to the monitoring of patients suffering from the stroke of unclear origin with increased risk of atrial arrhythmias progressing to atrial fibrillation. Atrial arrhythmias, especially atrial fibrillation, are associated with different severe health conditions (such as heart failure) and are frequently reported health problems especially in elderly people (aged >65 years), thus, the application area of the system is rather wider that monitoring of patients after stroke. The system consists of the following parts at least:

Equipment Designed for a Patient:
　patient coupled device (1),
　patient's smart device (2),
Equipment Designed for a Physician:
　physician's smart device (3), The system among the above-mentioned devices consists of a server with integrated modules for characterisation of time aggregation of the episodes of atrial arrhythmia (4), infrastructure of internet network, technical means ensuring connections between the said devices for data exchange.

Figure 2:
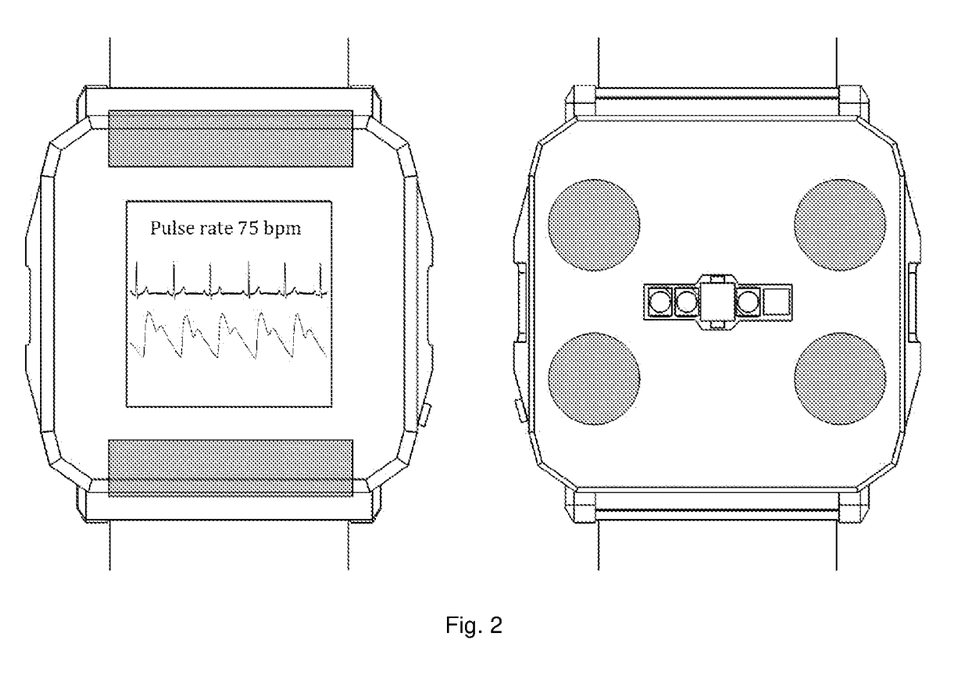
FIG. 2. Illustrates the view of main components of the patient coupled device.
Figure 4:
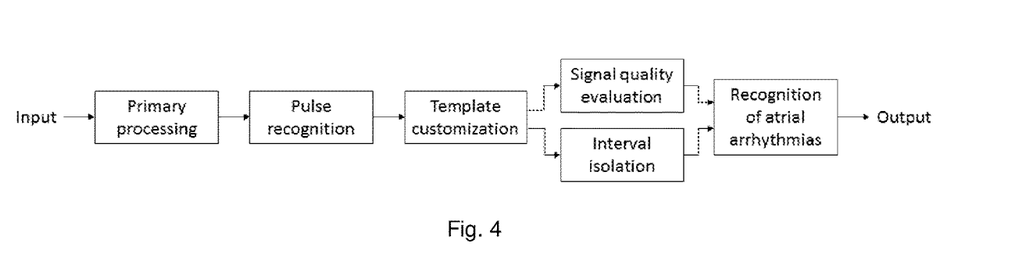
FIG. 4. A simplified block scheme of a module for atrial arrhythmia detection based on photoplethysmogram signal designed for integration in a patient coupled device.

A patient coupled portable device (1) (FIG. 2)—a device which is able to detect atrial arrhythmias in a real time from a continuously recorded photoplethysmogram signal and to perform other functions characteristic for such devices, e.g. recording of instantaneous pulse, step counting, assessment of recovery heart rate etc. A patient coupled device (1) is usually attached to a hand, however, it can be attached to other body parts (e.g. forearm, leg, head, ear, etc.). A smart bracelet, a smartwatch, a smart headphone, a smart headband and other smart devices having the above mention functions can be used instead. The software modules for atrial arrhythmia detection in photoplethysmogram signal are installed in a patient coupled device (1) or in a separate controlling smart device (2) (FIG. 4). A portable device (1) transfers data to a served during the period of device charging through the USB port of a computer or a device performing similar functions. A patient coupled device performs the following functions:

Analysis in the real time the photoplethysmogram signal and detects changes of pulse sequences caused by atrial arrhythmia.
　After automatic detection of atrial arrhythmias, the system user is advised to touch the electrodes integrated in the portable device and to record a short-term electrocardiogram signal.
　When the system user touches the integrated electrodes in the specified sequence, an up to 6-leads electrocardiogram signal (modified I, II, III, aVR, aVL, aVF) is recorded.
　If the atrial episodes are detected, data are sent to the server for further analysis.

Figure 3:
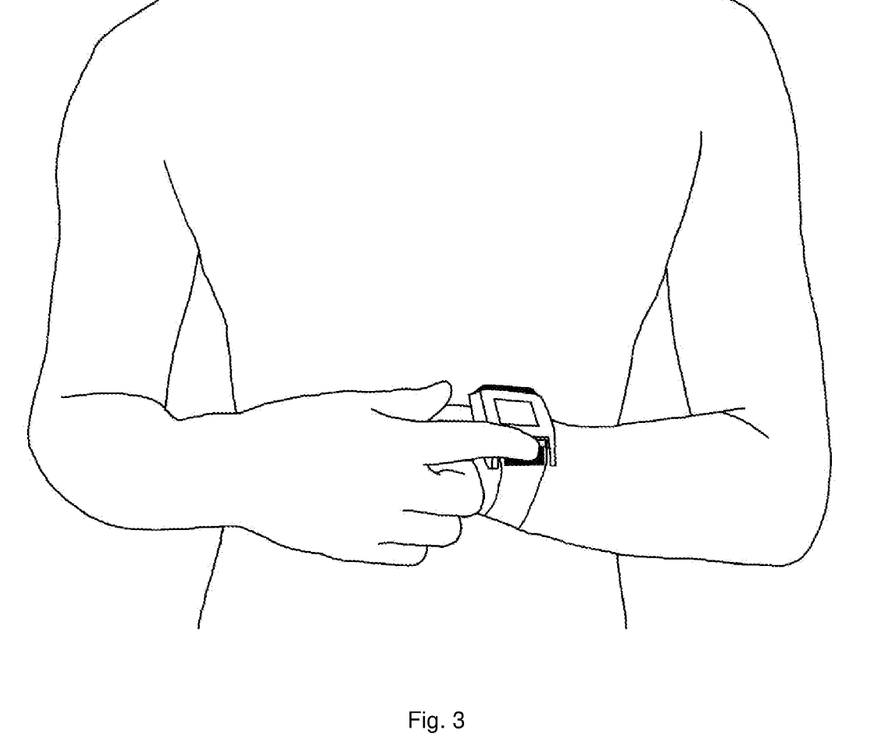
FIG. 3. Presents one of the options of the device use, designed to record 6-lead electrocardiogram not utilising the sticky electrodes.

The internal electrode of the portable device is in the continuous contact with the skin of wrist to which it is attached. The external electrodes are isolated from the internal electrode and for the registration of electrocardiogram signal they must be in contact with a finger of the other hand or with other body part, such as chest, abdomen or leg (FIG. 3). The recorded electrocardiogram signals are processed by the algorithms of digital signal processing installed in the portable device and specially designed to detect atrial arrhythmia in the short noisy electrocardiogram signals. When the rhythm disorder is detected, an electrocardiogram signal is sent to the server for storage, visualisation and physician information.

The algorithm for detection of atrial arrhythmia and a long-term monitoring of arrhythmia progression is resistant to movement artefacts in photoplethysmogram and to commonly reported innocuous rhythm disorders (FIG. 4). For this purpose, a photoplethysmography signal quality assessment block, a premature ventricle contraction filtration block and a bigeminy episode suppression block as well as sinus arrhythmia suppression block were implemented. The listed solutions improving reliability of atrial arrhythmia detection can be used in other portable devices having the heart contraction recording function. Atrial arrhythmias are detected considering distinctive features characteristic for specific arrhythmia type, such as atrial fibrillation is detected by irregular rhythm, atrial flutter—by a regular heart rhythm up to 150 beats per minute with abrupt onset and termination, ectopic short-term atrial tachycardia—by regular heart rate of 150-220 beats per minute with abrupt onset and termination.

The functions of patient's smart device can be carried out by different smart devices (e.g. by a smartphone, a tablet computer, a smartwatch, etc.) equipped with technical means required to maintain connections with internet network and installed software ensuring data exchange with the system server (4). The patient's smart device (2) by Internet connection (using https and/or other technologies) receives information about physician's decision which is made by the physician after receiving in his/her smart device (3) the information that is processed in the server (4).

The functions of physician's smart device (3) can be carried out by different smart devices (e.g. by a smartphone, a tablet computer, a smartwatch, etc.) equipped with technical means required to maintain connections with internet network and installed software ensuring data exchange with the system server (4). Physician's smart device (3) using Internet connection (https and/or other technologies) connects to the server with installed system software analysing of time distribution of the atrial arrhythmia episodes and ensuring data exchange between the devices visualisation of data as well as report developing. By the use of this system the physician receives detailed information about manifestation of atrial arrhythmia during a long-term monitoring, their distribution, progress and association with patent's behaviour (e.g. physical activity, body position etc.) and physiological condition (such as sleep, stress).

Figure 5:
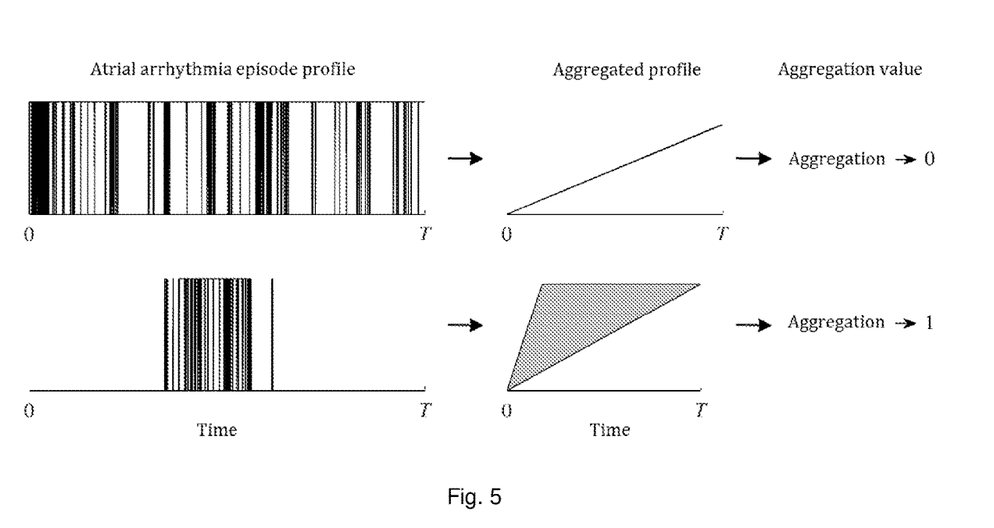
FIG. 5. A module for characterisation of time aggregation of the episodes of atrial arrhythmias designed for server or a smart device (e.g., smartphone, tablet computer, smartwatch etc.).

A software module of the server (4) analysis the distribution of atrial arrhythmia episodes profile detected by a long-time worn portable device and presents quantitative arrhythmia profile characterising parameters, such as aggregation of episode distribution, arrhythmia intensity, relative total duration, etc. (FIG. 5). A distribution profile of the atrial arrhythmia episodes can be quantitative evaluated within one day, week, month or year:

A duration of atrial arrhythmia indicates a proportional part of time when a person is in arrhythmia condition as compared with the entire monitoring period.
　Intensity of atrial arrhythmia episodes indicates the average number of arrhythmia episodes during a specified time unit (e.g. day, week, month).
　Aggregation of atrial arrhythmias characterises a profile of the time distribution of atrial arrhythmia episodes. Aggregation parameter considers whether the episodes of atrial arrhythmia are aggregated in a certain time interval, or are evenly distributed in the entire monitoring time interval. In this way aggregation parameter takes into account inter-distribution and inter-association between different arrhythmia types (e.g., atrial extra-systoles, a short-term ectopic tachycardia, atrial flutter and atrial fibrillation). Aggregation values around 0 indicate a low arrhythmia time concentration, which is characteristic for atrial arrhythmia profile, when arrhythmia episodes are equally distributed within the entire monitoring period. Aggregation values around 1 indicate a high arrhythmia time concentration, which is characteristic for atrial arrhythmia profiles, when a single short atrial arrhythmia episode is recorded within the entire monitoring period. Differently from proposed atrial fibrillation density (Charitos E. I. et al. A comprehensive evaluation of rhythm monitoring strategies for the detection of atrial fibrillation recurrence: insights from 647 continuously monitored patients and implications for monitoring after therapeutic interventions, Circulation, 126(7), 806-814, 2012), value of aggregation depends on the episode duration, i.e. with prolonged episode duration the value of aggregation parameter declines.

The server's software modules develop a report and send a message to physician's smart device. Technical means ensuring protection of users' data are also installed in the server.

The description of the most suitable options for invention implementation is presented aiming to illustrate and describe this invention. This is not a comprehensive or restricting description, designed to define the exact implementation form or version. The above presented description should be considered as an illustration rather than a restriction. The implementation version was selected and described for the professionals with the intention to help them understand the principles and best practical application of this invention with different modifications. It is expected that the extent of invention is defined by the enclosed claims and their equivalents, in which all mentioned terms have a broad meaning, except stated otherwise.

The embodiments described by the specialists may include any suggested changes, not deviating from the scope of this invention, as stated in the following claims.

What is claimed is:

1. A non-invasive method for long-term heart arrhythmia monitoring and time-distribution characterization, comprising steps of:
   a) providing a wrist-wearable device comprising a photoplethysmogram sensor configured to continuously record real-time photoplethysmogram signals, and an inner electrode configured to be in contact with a patient's wrist skin and at least two electrodes embedded on an external surface of the device and being isolated from the inner electrode and from the wrist skin and configured to be brought in contact with a body part for measurement of an electrocardiogram signal;
   b) the device continuously recording the real-time photoplethysmogram signals and detecting distinctive features of atrial arrhythmias by analyzing the real time photoplethysmogram signals;
   c) in response to detecting distinctive features of atrial arrhythmias in the real-time photoplethysmogram signals, the wrist-wearable device providing a notification or an alert via a user interface to the patient to record an electrocardiogram signal of 6-leads including modified I, II, III, aVR, aVL, and aVF using the wrist-wearable device by simultaneously touching one of the at least two electrodes embedded on the external surface of the device with a finger of the patient's other hand and touching a second electrode embedded on the external surface of the device with the chest, abdomen or leg of the patient's body;
   d) in response to the patient recording the electrocardiogram according to instructions of step c) the recorded electrocardiogram signal data being analyzed in the wrist-wearable device or sent to a server and analyzed in the server or in a smart device to detect atrial arrhythmias and to determine a time-aggregation value associated with an arrhythmia episode pattern, wherein the time-aggregation value is an estimate of time distribution based on arrythmia episode aggregation, arrhythmia intensity and relative total duration of the detected atrial arrhythmia episodes during a long-term monitoring period; and
   e) transferring at least the determined time aggregation value of step d) into a database useful for further analysis; wherein
      detection of the atrial arrhythmia distinctive features from the photoplethysmogram signal in step b) comprises detecting an irregular rhythm, detecting a heart rhythm up to 150 beats per minute with abrupt onset and termination, and detecting a heart rate of 150-220 beats per minute with abrupt onset and termination, wherein the detected irregular rhythm is indicative of atrial fibrillation; the detected heart rhythm up to 150 beats per minute with abrupt onset and termination is indicative of atrial flutter; and the detected heart rate of 150-220 beats per minute with abrupt onset and termination is indicative of short-term ectopic atrial tachycardia.

2. The method according to claim 1, wherein the notification or alert to the patient to record an electrocardiogram signal comprises providing short vibration from the wrist-wearable device or an indication on a monitor of the wrist-wearable device.

3. The method according to claim 1, wherein in response to detection of the atrial arrhythmia episode in the 6-lead electrocardiogram signal the 6-lead electrocardiogram signal data is sent to a physician's smart device or to the server.

4. The method according to claim 1, wherein a patient's smart device is coupled to the wrist-wearable device, wherein the patient's smart device is configured to connect to the server and/or the internet, and wherein the patient's smart device is configured to receive information from a physician's smart device.

5. The method according to claim 1, wherein the detection of atrial arrhythmia distinctive features from the photoplethysmogram signal comprises:
   assessing photoplethysmography signal quality;
   filtering a premature ventricle contraction signal;
   suppressing a bigeminy episode suppression signals; and
   suppressing sinus arrhythmia signals.

6. The method according to claim 1, further comprising presenting quantitative arrhythmia profile characterizing parameters.

7. The method according to claim 1, wherein analyzing the recorded electrocardiogram signal data to detect atrial arrhythmias and to determine a time-aggregation value associated with an arrhythmia episode pattern comprises:
   aggregating an arrhythmia episode time distribution;
   determining a frequency and duration of the detected episodes of atrial arrhythmia during the long-time monitoring period; and
   determining a time-aggregation value comprising total duration and frequency of episodes of atrial arrhythmia relative to a total duration of the long-time monitoring period.

8. The method according to claim 6, wherein the long-time monitoring period comprises one or more days, weeks, or months.

9. The method according to claim 7, wherein the time-aggregation value is closer to 0 than to 1 indicating low arrhythmia time concentration characteristic for atrial arrhythmia when arrhythmia episodes are equally distributed within an entire monitoring period, and closer to 1 than to 0 indicating a high arrhythmia time concentration characteristic for atrial arrhythmia profile when a single short atrial arrhythmia episode is recorded within the entire monitoring period.

10. Performing the method of claim 1 using a system for long-time monitoring and characterization of atrial arrhythmias according to the method of claim 1, comprising:

providing a wrist-wearable device comprising a photoplethysmogram sensor configured to continuously record real-time photoplethysmogram signals, and an inner electrode configured to be in contact with a patient's wrist skin and at least two electrodes embedded on an external surface of the device and being isolated from the inner electrode and from the wrist skin and configured to be brought in contact with a body part for measurement of an electrocardiogram signal;

a patient's smart device coupled to the wrist-wearable device configured to connect to a server and/or the internet;

a physician's smart device configured to receive information from the patient's smart device; and the server configured for data transfer between the wrist-wearable device and the smart devices, for data storage, and for processing, visualization and report development.

11. The system according to claim 10, wherein the wrist-wearable device is configured to provide a notification or an alert via a user interface wherein the notification or alert comprises short tactile vibration of the device, an indication on a monitor of the device, or combinations thereof.

12. The system according to claim 10, wherein the at least two electrodes embedded on an external surface of the device are located on top of the wrist-wearable device and the wrist-wearable device is configured to receive a signal of simultaneous contact of the at least two electrodes and the inner electrode, when one of the at least two electrodes is contacted by a finger of the patient, a second of the at least two electrodes is simultaneously contacted by one of chest, abdomen, or leg of the patient, and the inner electrode is in contact with wrist skin of the patient, and in response to receiving a signal of simultaneous contact of the inner electrode and the at least two electrodes embedded on an external surface of the device the wrist-wearable device is configured to record 6-leads electrocardiogram signals including modified I, II, III, aVR, aVL, and aVF.

13. A non-invasive method for long-term heart arrhythmia monitoring and time-distribution characterization, comprising steps of:
a) providing a wrist-wearable device comprising a photoplethysmogram sensor configured to continuously record real-time photoplethysmogram signals, and an inner electrode configured to be in contact with a patient's wrist skin and at least two electrodes embedded on an external surface of the device and being isolated from the inner electrode and from the wrist skin and configured to be brought in contact with a body part for measurement of an electrocardiogram signal;
b) the device continuously recording the real-time photoplethysmogram signals and detecting distinctive features of atrial arrhythmias by analyzing the real time photoplethysmogram signals;
c) in response to detecting distinctive features of atrial arrhythmias in the real-time photoplethysmogram signals, the wrist-wearable device providing a notification or an alert via a user interface to the patient to record an electrocardiogram signal of 6-leads including modified I, II, III, aVR, aVL, and aVF using the wrist-wearable device by simultaneously touching one of the at least two electrodes embedded on the external surface of the device with a finger of the patient's other hand and touching a second electrode embedded on the external surface of the device with the chest, abdomen or leg of the patient's body;
d) in response to the patient recording the electrocardiogram according to instructions of step c) the recorded electrocardiogram signal data being analyzed in the wrist-wearable device or sent to a server and analyzed in the server or in a smart device to detect atrial arrhythmias and to determine a time-aggregation value associated with an arrythmia episode pattern, wherein the time-aggregation value is an estimate of time distribution based on arrythmia episode aggregation, arrhythmia intensity and relative total duration of the detected atrial arrhythmia episodes during a long-term monitoring period; and
e) transferring at least the determined time aggregation value of step d) into a database useful for further analysis; wherein
analyzing the recorded electrocardiogram signal data to detect atrial arrhythmias and to determine a time-aggregation value associated with an arrhythmia episode pattern comprises:
aggregating an arrhythmia episode time distribution;
determining a frequency and duration of the detected episodes of atrial arrhythmia during the long-time monitoring period; and
determining a time-aggregation value comprising total duration and frequency of episodes of atrial arrhythmia relative to a total duration of the long-time monitoring period, wherein the time-aggregation value closer to 0 than to 1 indicates low arrhythmia time concentration characteristic for atrial arrhythmia when arrhythmia episodes are equally distributed within an entire monitoring period, and the value closer to 1 than to 0 indicates a high arrhythmia time concentration characteristic for atrial arrhythmia profile when a single short atrial arrhythmia episode is recorded within the entire monitoring period.

* * * * *